United States Patent [19]
Barthelemy et al.

[11] Patent Number: 5,366,946
[45] Date of Patent: Nov. 22, 1994

[54] STABILIZED 1,1-DICHLORO-1-FLUOROETHANE, PREMIXTURES INTENDED FOR THE PREPARATION OF POLYMERIC FOAMS AND POLYMERIC FOAMS OBTAINED BY THE USE THEREOF

[75] Inventors: Pierre Barthelemy, Pietrebais; Mireille Paulus, Brussels; Annie Leroy, Fauvillers, all of Belgium

[73] Assignee: Solvay (Société Anonyme), Brussels,

[21] Appl. No.: 125,186

[22] Filed: Sep. 23, 1993

[30] Foreign Application Priority Data

Sep. 29, 1992 [BE] Belgium .................. 09200849

[51] Int. Cl.$^5$ .................................. B01J 31/00
[52] U.S. Cl. ........................ 502/167; 252/182.24; 252/182.29; 252/393; 252/394; 252/396; 502/169; 502/500; 521/123; 521/174
[58] Field of Search .......... 252/393, 394, 396, 182.29, 252/182.24; 502/500; 521/174, 123

[56] References Cited

U.S. PATENT DOCUMENTS

| | | | |
|---|---|---|---|
| 4,803,009 | 2/1989 | Gorski | 252/171 |
| 4,863,630 | 9/1989 | Swan et al. | 252/171 |
| 4,894,176 | 1/1990 | Swan et al. | 252/171 |

FOREIGN PATENT DOCUMENTS

| | | |
|---|---|---|
| 0421790A2 | 4/1991 | European Pat. Off. . |
| 91/13969 | 9/1991 | WIPO . |
| 91/14020 | 9/1991 | WIPO . |
| 92/10453 | 6/1992 | WIPO . |

OTHER PUBLICATIONS

Chemical Abstracts, vol. 111, No. 25, Dec. 18, 1989, Columbus, Ohio, US; abstract No. 232060h, Masato Fukushima et al "Stabilization of hydrogen–containing fluorocarbons" & JP-A-01128945 (Asahi Glass).

*Primary Examiner*—Morton Foelak
*Attorney, Agent, or Firm*—Spencer, Frank & Schneider

[57] ABSTRACT

Compositions consisting essentially of 1,1-dichloro-1-fluoroethane and at least one stabilizing agent chosen from epoxides and hydrocarbons substituted by a nitro group. These compositions can especially be used as cleaning agent and as blowing agent for polyurethane foams.

14 Claims, No Drawings

STABILIZED 1,1-DICHLORO-1-FLUOROETHANE, PREMIXTURES INTENDED FOR THE PREPARATION OF POLYMERIC FOAMS AND POLYMERIC FOAMS OBTAINED BY THE USE THEREOF

The present invention relates to the stabilization of 1,1-dichloro-1-fluoroethane.

Entirely halogenated chlorofluorinated hydrocarbons (CFCs) suspected of having a harmful effect on the ozone layer can be substituted in many applications, such as, for example, use as a blowing agent for the preparation of foams, as a liquid coolant or as a propellant, by fluorinated hydrocarbons comprising at least one hydrogen atom, also called hydrofluoroalkanes (HFAs). 1,1-Dichloro-1-fluoroethane (HFA-141b) is a hydrofluoroalkane which is proving to be a useful substitute of certain CFCs, especially as a blowing agent for polymeric foams or as a cleaning agent.

It is generally recognised that compositions comprising hydrofluoroalkanes must be stabilized to prevent any risk of degradation during storage or use, more particularly when they are used as a cleaning agent and when they contain various organic compounds, especially lower alcohols, intended to improve their solvent properties. Thus it has already been proposed to add nitromethane and/or 1,2-epoxybutane and/or diisopropylamine and/or 4-methoxyphenol to azeotropic or pseudoazeotropic compositions of 1,1-dichloro-1-fluoroethane in a mixture with 1,1,1-trifluoro-2,2-dichloroethane (HFA-123) and, optionally, with lower alcohols, in order to stabilize them against degradation by oxidation, by polymerization or by interaction of the components during storage or during use of these compositions (Patent Applications EP-A-421,790 and WO 91/13969 of Du Pont De Nemours and WO 91/14020 of Allied-Signal).

It has now been observed that 1,1-dichloro1-fluoroethane, even when it is not mixed with other hydrofluoroalkanes or with lower alcohols, can, under certain conditions, undergo degradation. It was observed that, even in very small amounts, Lewis acids of metal halide type can induce significant degradation of 1,1-dichloro-1-fluoroethane. Thus less than 1 ppm of iron chloride dissolved in the 1,1-dichloro-1-fluoroethane is sufficient to affect the quality of the product in an unacceptable way, even at room temperature. Additionally, it has further been observed that 1,1-dichloro-1-fluoroethane containing traces of Lewis acids of metal halide type proves to be very corrosive to metal surfaces.

It was also observed that, in the premixtures comprising polyols, intended for the manufacture of polyurethane foams, 1,1-dichloro-1-fluoroethane-undergoes a degradation which causes the appearance of harmful degradation products, especially 1-chloro-1-fluoroethane, vinylidene chloride and vinylidene chlorofluoride.

The invention is especially targeted at providing 1,1-dichloro-1-fluoroethane which is stabilized against degradation caused by Lewis acids of metal halide type. It is also targeted at making 1,1-dichloro-1-fluoroethane non-corrosive to metal surfaces in the presence of Lewis acids of metal halide type, especially when it is used as a cleaning agent for these surfaces.

Another object of the present invention is to provide premixtures for polyurethane or polyisocyanurate foams, comprising at least one polyol and 1,1-dichloro-1fluoroethane, of improved stability, in which the formation of degradation products of 1,1-dichloro1-fluoroethane is greatly inhibited.

The invention consequently relates to compositions consisting essentially of 1,1-dichloro-1-fluoroethane and at least one stabilizing agent of 1,1-di-chloro-1-fluoroethane, characterized in that the stabilizing agent is chosen from $C_3$–$C_8$ epoxides, $C_1$–$C_8$ hydrocarbons substituted by a nitro group and their mixtures.

The epoxides containing from 3 to 8 carbon atoms can be unsubstituted epoxides or epoxides substituted, for example, by halogens, by ether/oxide functional groups or by hydroxyl groups. Most often, epoxides chosen from 1,2-epoxypropane, epichlorohydrin, glycidol, epoxybutanes, epoxypentanes, 1,4-epoxycyclohexane, styrene oxide and the methyl, ethyl, propyl, isopropyl and tert-butyl glycidyl ethers are used. Vicihal epoxides containing from 3 to 5 carbon atoms are preferably chosen. Among the latter, it is particularly preferable to use 1,2-epoxypropane, 1,2-epoxybutane, glycidol or epichlorodyrin. 1,2-Epoxypropane and 1,2-epoxybutane have been found to be particularly suitable.

It is possible to use, as $C_1$–$C_8$ hydrocarbons substituted by a nitro group, nitroalkanes containing from i to 6 carbon atoms and aromatic hydrocarbons containing from 6 to 8 carbon atoms. The hydrocarbons substituted by a nitro group are advantageously chosen from nitromethane, nitroethane, nitropropanes, nitrobutanes, nitropentanes, nitrohexanes and nitrobenzenes. Nitroalkanes are preferably chosen. Among the latter, nitromethane, nitroethane, 1-nitropropane or 2-nitropropane are particularly preferred. Nitromethane is very particularly preferred.

In the compositions according to the invention, the stabilizing agent must be used in an amount suitable for stabilizing the 1,1-dichloro-1-fluoroethane. The optimum amount of stabilizing agent to be used depends on various parameters, among which are the stabilizing agent selected and the application for which the composition is intended. In practice, there is generally used at least approximately 0.01% by weight of each stabilizing agent with respect to the total weight of the composition. Preferably, at least approximately 0.05% thereof is used. In a particularly preferred way, at least approximately 0.1% thereof is used. Moreover, the maximum does not usually exceed approximately 5% by weight of each stabilizing agent with respect to the total weight of the composition. Preferably, the maximum does not exceed approximately 2%.

The compositions according to the invention can contain a number of stabilizing agents selected from epoxides and hydrocarbons substituted by a nitro group. When such is the case, the compositions according to the invention preferably contain both an epoxide and a hydrocarbon substituted by a nitro group. As a variant, other stabilizing agents can also be added to the stabilized compositions according to the invention.

The compositions according to the invention consist essentially of 1,1-dichloro-1-fluoroethane and of the stabilizing agents as defined above. They can optionally contain, in a limited amount, constituents other than 1,1-dichloro-1-fluoroethane and stabilizing agents. Thus it is that the compositions according to the invention can contain hydrofluoroalkanes other than 1,1-dichloro-1-fluoroethane in a total amount which does not exceed 0.5 % of the weight of the 1,1-dichloro-1-fluoroethane. The compositions according to the invention can also contain impurities of the stabilizing agent and unsaturated impurities of the 1,1-dichloro-1-fluoroethane, such as, for example, 1,1-dichloroethylene and iron(III) chloride in a total amount not exceeding 2% of the weight of the 1,1-dichloro-1-fluoroethane.

It was observed that the use of a $C_3$–$C_8$ epoxide or of a $C_1$–$C_8$ hydrocarbon substituted by a nitro group as stabilizing agent of 1,1-dichloro-1-fluoroethane against degradation induced by Lewis acids of metal halide type leads to excellent results. Addition to 1,1-dichloro1-fluoroethane of such an epoxide or of such a hydrocarbon substituted by a nitro group, even in an amount of less than 5% of the weight of the 1,1-dichloro-1-fluoroethane, strongly inhibits degradation of the product in the presence of Lewis acids of metal halide type.

The compositions according to the invention are shown to be stable in the presence of Lewis acids of metal halide type, such as, especially, iron(III) chloride, iron(II) chloride and aluminium chloride, whether these acids are present in minute amounts, for example the order of 0.1 mg per kilo or 1,1-dichloro-1-fluoroethane, or in larger amounts, for example of the order of several hundreds of mg per kilo of 1,1-dichloro-1-fluoroethane. Excellent results are obtained when the compositions based on 1,1-dichloro-1-fluoroethane are in the presence of an amount of Lewis acids of metal halide type of between approximately 0.5 and 500 mg per kilo of hydrofluoroalkane. Very good results are also obtained when a composition according to the invention based on 1,1-dichloro-1-fluoroethane is in the presence of significant amounts of Lewis acids of metal halide type, of the order of 1 gram or more of Lewis acids per kilo of 1,1-dichloro-1-fluoroethane.

It was also observed that the use of a $C_1C_8$ epoxide or a $C_1$–$C_8$ hydrocarbon substituted by a nitro group as stabilizing agent of 1,1-dichloro-1-fluoroethane against degradation induced by polyols in the premixtures intended for the preparation of polyurethane foams leads to excellent results.

The compositions according to the invention can advantageously be used in conventional applications where the hydrofluoroalkanes replace trichlorofluoromethane, particularly as cleaning agent or as blowing agent for the preparation of polymeric foams.

As cleaning agent, the compositions according to the invention are especially suitable as solvent or as degreasing agent in any cold cleaning operation or cleaning operation of surfaces with vapour. They are also appropriate as defluxing agents in the cleaning processes of printed circuit boards, processes intended to remove, from the surface of these boards, the soldering flux used in the soldering stage of the electronic components and its residues. They can also be used as desiccative agents, that is to say for removing the water adsorbed on the surface of solid objects requiring a perfectly clean surface, such as printed circuits, silicon wafers, lenses, watch-making components and any other precision parts.

As blowing agent, the stabilized compositions according to the invention can in particular be used for the preparation of polyurethane or polyisocyanurate foams.

The invention also relates to premixtures intended for the preparation of polyurethane or polyisocyanurate foams, comprising at least one polyol and at least one blowing agent, in which the blowing agent essentially consists of a composition consisting essentially of 1,1-dichloro-1-fluoroethane and at least one stabilizing agent of the 1,1-dichloro-1-fluoroethane chosen from epoxides and hydrocarbons substituted by a nitro group, as defined above.

The invention particularly relates to premixtures which comprise at least one polyol and which are intended for the manufacture of polyurethane foams. A large range of polyols, already disclosed in the prior art, can be used in the premixtures according to the invention, such as polyether polyols and polyester polyols. The proportion of blowing agent with respect to the polyol in the premixtures will vary, especially depending on the application, the type of foam prepared, the nature of the polyol and also depending on other parameters. It can be easily determined in each particular case. In practice, there is generally used from 1 to 50 parts by weight of the stabilized composition according to the invention per 100 parts by weight of polyol. Excellent results were obtained with premixtures intended for the manufacture of rigid polyurethane foams. These premixtures have proved to be particularly stable, in particular giving rise only to very low formation of 1-chloro-1-fluoroethane. Such premixtures can optionally comprise one or more other blowing agents, in addition to the stabilized 1,1- dichloro-1-fluoroethane according to the invention. However, 1,1-dichloro-1-fluoroethane is the only hydrofluoroalkane included in the premixtures according to the invention.

These premixtures can optionally consist only of the suitable amounts of polyol and of stabilized composition according to the invention. However, as a general rule, they comprise, besides suitable amounts of polyol and of stabilized composition according to the invention, suitable amounts of surfactants, catalysts, flame-retardant agents and optionally other additives commonly used to prepare polyurethane foams by reaction with polyisocyanates.

The invention also relates to polyurethane or polyisocyanurate foams obtained by use of a composition or premixture in accordance with the invention, as defined above.

The invention is illustrated, in a non-limiting way, by the examples below. Examples 2, 3, 5 and 6 are in accordance with the invention. Examples 1 and 4, notated "C", are given by way of comparison.

EXAMPLES 1C, 2 and 3

1,1-Dichloro-1-fluoroethane saturated with $FeCl_3$, to which various stabilizing agents have been added, was boiled at reflux in a round-bottomed distillation flask equipped with a Soxhlet extractor and a reflux condenser, in the presence of metal test pieces made of Thomas steel, one placed in the distillation flask, a second in the Soxhlet extractor and a third in the reflux condenser. The metal test pieces had an overall surface area of 832 mm². The corrosiveness of the stabilized 1,1-dichloro-1-fluoroethane compositions was evaluated by measuring the loss in weight of the test pieces, after 7 days. The results are collated in Table I.

TABLE I

|  | Ex. 1C | Ex. 2 | Ex. 3 |
|---|---|---|---|
| Stabilizing agent (in g per 100 ml of HFA-141b) | | | |
| Nitromethane | — | — | 1 |
| Epoxybutane | — | 1 | 1 |
| Losses in weight | | | |

TABLE I-continued

|  | Ex. 1C | Ex. 2 | Ex. 3 |
| --- | --- | --- | --- |
| (g/m² · day) | | | |
| Round-bottomed flask | 0.51 | 0.01 | 0.01 |
| Soxhlet | 0.72 | 0.05 | 0.03 |
| Reflux condenser | 2.21 | 0.06 | 0.05 |
| Total loss | 3.44 | 0.12 | 0.09 |

EXAMPLE 4C

A premixture for the preparation of polyurethane foams was prepared according to the following composition by weight:

50 parts by weight of Arcol 3770 amino polyol from Arco 50 parts by weight of Voranol RA 640 amino polyol from Dow 1 part by weight of water 2 parts by weight of B 1048 silicone surfactant from Goldschmidt 2 parts by weight of N-methylmorpholine 1.5 parts by weight of N,N-dimethylcyclohexylamine 24 parts by weight of 1,1-dichloro-1-fluoroethane A predetermined amount of this mixture was enclosed in a glass flask maintained at a constant temperature of 50° C. for 12 days.

A sample was then removed and the degradation products of the 1,1-dichloro-1-fluoroethane were analyzed by gas phase chromatography. The main degradation products formed are vinylidene chlorofluoride (VCF), vinylidene chloride (VF2) and 1-chloro-1-fluoroethane (HFA-151a). The results are shown in Table II.

EXAMPLES 5 and 6

Variable amounts of various stabilizing agents were added, before ageing, to a premixture identical to that of Example 4C so as to produce premixtures in accordance with the invention.

After ageing under conditions identical to those of Example 4C, the degradation products of the 1,1-dichloro-1-fluoroethane were analyzed by gas phase chromatography. The results are also shown in Table II.

By comparison with Example 4C, Examples 5 and 6 according to the invention illustrate that the amount of degradation products formed, particularly of 1-chloro1-fluoroethane, is very markedly less and thus that the stability of the 1,1-dichloro-1-fluoroethane is very substantially improved in the premixtures according to the invention.

TABLE II

| | Stabilizing compound | | Degradation products of HFA-141b (mg/kg HFA-141b) | | |
| --- | --- | --- | --- | --- | --- |
| Example | Nature | Amount (weight % of HFA-14b) | VCF | VC2 | HFA-151a |
| 4C | — | — | 92 | 131 | 294 |
| 5 | Nitromethane | 0.1% | 72 | 37 | 6 |
| 6 | Nitromethane | 0.05% | 77 | 50 | 17 |

We claim:

1. A composition consisting essentially of 1,1-dichloro-1-fluoroethane, at least one halide Lewis acid and at least one stabilizing agent for 1,1-dichloro-1-fluoroethane, selected from the group consisting of $C_3$–$C_8$ epoxides, $C_1$–$C_8$ hydrocarbons substituted by a nitro group and mixtures thereof.

2. The composition according to claim 1, including approximately 0.05% by weight of said stabilizing agent.

3. The composition according to claim 1, including approximately 0.1% by weight of stabilizing agent.

4. The composition according to claim 1, including both an epoxide and a hydrocarbon substituted by a nitro group.

5. The composition according to claim 4, including from approximately 0.01 to approximately 5% by weight of each stabilizing agent with respect to the total weight of the composition.

6. The composition according to claim 1, including approximately 1 g of each of said at least one stabilizing agent per 100 ml of 1,1-dichloro-1-fluoroethane.

7. The composition according to claim 1, wherein the stabilizing agent is chosen from vicinal epoxides containing from 3 to 5 carbon atoms.

8. The composition according to claim 7, wherein the stabilizing agent is chosen from 1,2-epoxypropane and 1,2-epoxybutane.

9. The composition according to claim 1, wherein the stabilizing agent is chosen from nitroalkanes containing from 1 to 6 carbon atoms and aromatic hydrocarbons substituted by a nitro group and containing from 6 to 8 carbon atoms.

10. The composition according to claim 1, wherein the stabilizing agent is chosen from nitromethane, nitroethane, 1-nitropropane and 2-nitropropane.

11. A composition consisting essentially of at least one polyol, and from approximately 0.01% to approximately 5% by weight, compared to the weight of the composition, of 1,1-dichloro-1-fluoroethane, at least metal halide Lewis acid, and at least one stabilizing agent for 1,1-dichloro-1-fluoroethane, selected from the group consisting of $C_3$–$C_8$ epoxides, $C_1$–$C_8$ hydrocarbons substituted by a nitro group, and mixtures thereof.

12. The composition set forth in claim 11, including approximately 0.1% by weight, compared to the weight of the composition, of said stabilizing agent.

13. The composition set forth in claim 11, including approximately 0.05% by weight, compared to the weight of the composition, of said stabilizing agent.

14. The composition set forth in claim 11, wherein said stabilizing agent includes both an epoxide selected from the group consisting of $C_3$–$C_8$ epoxides, and a $C_1$–$C_8$ hydrocarbon substituted by a nitro group.

* * * * *